United States Patent
Kuo et al.

(10) Patent No.: US 9,423,359 B2
(45) Date of Patent: Aug. 23, 2016

(54) WAFER CHARGING ELECTROMAGNETIC INSPECTION TOOL AND METHOD OF USING

(71) Applicant: TAIWAN SEMICONDUCTOR MANUFACTURING COMPANY, LTD., Hsinchu (TW)

(72) Inventors: Ming-Sung Kuo, Zhubei (TW); Chiun-Chieh Su, Hsinchu (TW); Chih-Shun Chu, Hsinchu (TW); To-Yu Chen, Tu-Ku Town (TW)

(73) Assignee: TAIWAN SEMICONDUCTOR MANUFACTURING COMPANY, LTD. (TW)

( * ) Notice: Subject to any disclaimer, the term of this patent is extended or adjusted under 35 U.S.C. 154(b) by 277 days.

(21) Appl. No.: 13/927,693

(22) Filed: Jun. 26, 2013

(65) Prior Publication Data
US 2015/0002835 A1 Jan. 1, 2015

(51) Int. Cl.
G01N 21/95 (2006.01)
H01L 21/66 (2006.01)
G01N 21/33 (2006.01)
G01N 21/47 (2006.01)
G01N 21/55 (2014.01)

(52) U.S. Cl.
CPC .......... *G01N 21/9501* (2013.01); *H01L 22/12* (2013.01); *G01N 21/33* (2013.01); *G01N 21/4788* (2013.01); *G01N 21/55* (2013.01)

(58) Field of Classification Search
CPC ... G01N 21/33; G01N 21/4788; H01L 22/12
See application file for complete search history.

(56) References Cited

U.S. PATENT DOCUMENTS

| | | | | |
|---|---|---|---|---|
| 4,847,496 A | * | 7/1989 | Kamieniecki | G01R 29/24 250/315.3 |
| 5,189,481 A | * | 2/1993 | Jann et al. | 356/73 |
| 5,459,632 A | * | 10/1995 | Birang et al. | 361/234 |
| 6,140,131 A | * | 10/2000 | Sunakawa et al. | 436/72 |
| 6,583,634 B1 | * | 6/2003 | Nozoe | G01R 31/307 324/754.22 |
| 2003/0081201 A1 | * | 5/2003 | Shibata | G01N 21/33 356/237.2 |
| 2005/0139772 A1 | * | 6/2005 | Hasegawa et al. | 250/311 |
| 2005/0190310 A1 | * | 9/2005 | Koyama et al. | 349/5 |
| 2006/0089709 A1 | * | 4/2006 | Helmus | 623/1.44 |

FOREIGN PATENT DOCUMENTS

JP    2000180385 A  *  6/2000

OTHER PUBLICATIONS

George Wardly, "Electrostatic Wafer Chuch for Electron Beam Microfabrication", Review of Scientific Instruments 44, 1506 (1973).*

* cited by examiner

*Primary Examiner* — Michael A Lyons
(74) *Attorney, Agent, or Firm* — Hauptman Ham, LLP

(57) ABSTRACT

An electromagnetic inspection tool which includes a stage configured to support a wafer having a first surface and an emitter configured to emit electromagnetic waves to be incident on the first surface. The electromagnetic inspection tool further includes a detector configured to detect electromagnetic waves returned from the first surface and a charging mechanism configured to charge the first surface. A method of electromagnetically inspecting a wafer which includes loading a wafer having a first surface onto a stage and emitting electromagnetic waves to be incident on the first surface. The method further includes detecting electromagnetic waves returned from the first surface and charging the first surface prior to detecting the electromagnetic waves returned from the first surface.

20 Claims, 5 Drawing Sheets

WAFER CHARGING ELECTROMAGNETIC INSPECTION TOOL AND METHOD OF USING

BACKGROUND

Inspection steps are interspersed throughout a semiconductor production process in order to monitor product quality and to identify and isolate problems which negatively impact a production yield. Inspection steps are performed using either electromagnetic detection, in which electromagnetic waves are incident on a device surface and an angle of reflection or refraction of the electromagnetic waves is detected, or electron beam (e-beam) inspection, in which a stream of electrons are incident on the device surface and electrons returned from the surface are detected. E-beam inspection is a more time consuming process than optical detection; however, e-beam inspection has higher resolution capabilities than optical detection.

As the processing node for semiconductor manufacturing decreases, the detection of abnormalities in features formed on a wafer using electromagnetic detection becomes more difficult because a signal-to-noise ratio (SNR) decreases to a point where differentiation between a detected signal and background noise is not precise. As the SNR approaches 1.0, the amount of noise is equal to the detected signal making differentiation between the two impossible.

BRIEF DESCRIPTION OF THE DRAWINGS

One or more embodiments are illustrated by way of example, and not by limitation, in the figures of the accompanying drawings, wherein elements having the same reference numeral designations represent like elements throughout. It is emphasized that, in accordance with standard practice in the industry various features may not be drawn to scale and are used for illustration purposes only. In fact, the dimensions of the various features in the drawings may be arbitrarily increased or reduced for clarity of discussion.

DETAILED DESCRIPTION

Figure 1A:
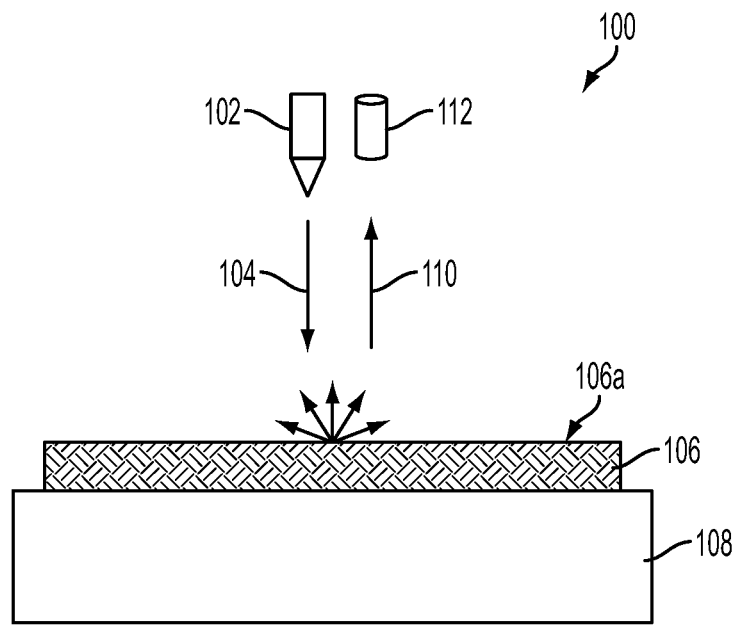
FIGS. 1A and 1B are high-level diagrams of an electromagnetic inspection tool in accordance with one or more embodiments.

The following disclosure provides many different embodiments, or examples, for implementing different features of the invention. Specific examples of components and arrangements are described below to simplify the present disclosure. These are examples and are not intended to be limiting.

A contrast of a signal obtained using an electromagnetic inspection tool is determined based on several factors including a wavelength of an electromagnetic wave incident on the wafer, a focal distance of a detector, an intensity of the electromagnetic wave incident on the wafer, an aperture of the emitter and a material of the wafer. The contrast of the signal is the signal-to-noise ratio (SNR). A higher contrast means a higher SNR, which will result in easier identification of abnormalities in a surface of the wafer. Adjustments to the wavelength, focal distance, intensity and aperture are able to provide a degree of control over the contrast of the detected signal. However, as the technology node decreases, the limits of these adjustments are being surpassed.

The material of the wafer surface is determined by the production process. However, a temporary change in the charge at the surface of the wafer will change the contrast detected during electromagnetic inspection. By adding electrons or holes at a surface of the wafer, the electromagnetic waves incident on the wafer interact with the charged surface of the wafer and increases contrast of the detected signal. The increased contrast allows determination of the contours of the wafer surface and detection of abnormalities having a feature size below a normal resolution of the electromagnetic inspection tool. Abnormalities are detected by comparing a target location on the wafer surface, such as a die, with an adjacent location which is processed to have a same structure. Identifying the differences between the target location and the adjacent location facilitates determining the presence of abnormalities.

In some embodiments, an amount of charge on the surface of the wafer is greater than 0 electron volt (eV) and in some embodiments ranges equal to or greater than 1 eV. In some embodiments, an amount of charge on the surface of the wafer ranges from about 1,000 eV to about 3,000 eV. If the amount of charge on the surface of the wafer is too high, structures on the wafer can be damaged, in some instances. In some embodiments, the amount of charge on the surface of the wafer ranges from about 2,000 eV to about 3,000 eV. This narrower range provides a higher degree of contrast with respect to the broader range and also maintains a low risk of damage to the wafer surface.

In some embodiments, the wafer surface is charged using a contact charging method. In some embodiments, the contact charging method includes at least one of direct contact charging, pin charging, electron gun charging, or other suitable methods which add electrons or holes to the wafer surface. In some embodiments, the wafer surface is charged using a contact-less charging method. In some embodiments, the contact-less charging method includes at least one of induction charging, capacitance charging, or other suitable methods which redistribute electrons or holes from within the wafer to the wafer surface.

FIG. 1A is a high-level diagram of an electromagnetic inspection tool 100 in accordance with one or more embodiments. In the arrangement of FIG. 1A, electromagnetic inspection tool 100 is configured to detect reflected light. Electromagnetic inspection tool 100 includes an emitter 102 configured to emit emitted electromagnetic waves 104 toward a wafer 106 supported on a stage 108. When emitted electromagnetic waves 104 are incident on a surface 106a of wafer 106, the surface reflects reflected electromagnetic waves 110 back to a detector 112. Detector 112 is configured to receive reflected electromagnetic waves 110 and output a detection signal to a computer for generating a defect map. The defect map provides information related to abnormalities on surface 106a along with a position of the abnormalities on wafer 106.

Figure 1B:
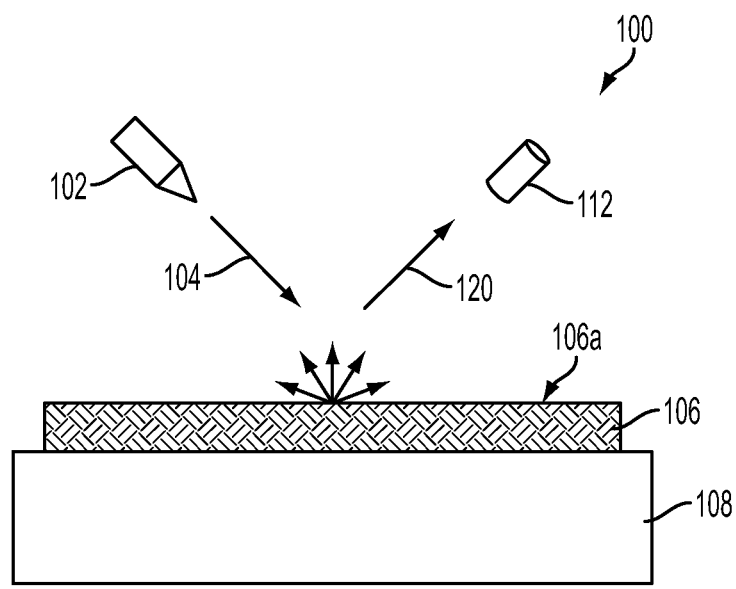

FIG. 1B is a high-level diagram of electromagnetic inspection tool 100 in accordance with one or more embodiments. In the arrangement of FIG. 1B, electromagnetic inspection tool 100 is configured to detect refracted and/or scattered electromagnetic waves. Similar to FIG. 1A, electromagnetic inspection tool 100 includes emitter 102 configured to emit electromagnetic wave 104 toward wafer 106 supported on stage 108. In contrast to FIG. 1A, when emitted electromagnetic waves 104 are incident on surface 106a, the surface refracts and/or scatters electromagnetic waves 120 back to detector 112. Detector 112 is configured to receive refracted and/or scattered electromagnetic waves 120 and output a detection signal to a computer for generating the defect map.

In some embodiments, a position of each of emitter 102 and detector 112 is adjustable so that a single electromagnetic inspection tool 100 is usable for both reflected electromagnetic wave detection and refracted electromagnetic wave detection. In some embodiments, electromagnetic inspection tool 100 is configured to inspect using reflected electromagnetic waves if a number of layers on wafer 106 is small, e.g., less than 5 micrometers (μm) in total thickness. In some embodiments, electromagnetic inspection tool 100 is configured to inspect using refracted and/or scattered electromagnetic waves if a number of layers on wafer 106 is large, e.g., equal to or greater than 5 μm in total thickness. In some embodiments, electromagnetic inspection tool 100 uses a combination of reflected electromagnetic wave detection and refracted and/or scattered electromagnetic wave detection on a same wafer. In some embodiments, stage 108 is configured to rotate wafer 106 to switch between reflected electromagnetic wave detection and refracted and/or scattered electromagnetic wave detection.

Emitter 102 is configured to emit electromagnetic waves having a wavelength equal or less than 700 nanometers (nm). In some embodiments, emitter 102 is configured to emit electromagnetic waves in the visible spectrum. In some embodiments, emitter 102 is configured to emit electromagnetic waves in the ultraviolet spectrum. In some embodiments, emitter 102 is configured to emit deep ultraviolet (DUV) electromagnetic waves in a wavelength range from about 193 nanometers (nm) to about 248 nm. In some embodiments, emitter 102 is configured to emit extreme ultraviolet (EUV) electromagnetic waves in a wavelength ranging from about 13.5 nm to about 193 nm. As the wavelength of emitted electromagnetic wave becomes shorter, smaller features on surface 106a are detectable. However, emitters configured to emit shorter wavelengths consume more energy than emitters configured to emit longer wavelengths. In some embodiments, emitter 102 is capable of adjusting a wavelength of emitted electromagnetic waves 104. In some embodiments, emitter 102 is configured to emit a single wavelength.

In some embodiments, emitter 102 comprises a laser. In some embodiments, the laser is a single wavelength laser. In some embodiments, the laser is a tunable laser capable of emitting a plurality of different wavelengths. In some embodiments, emitter 102 comprises a broad-band source configured to emit a variety of different wavelengths at a same time. In some embodiments where emitter 102 comprises a broad-band source, the emitter further comprises a filter configured to transmit a narrower wavelength-band to be incident on the wafer. In some embodiments, the filter is a tunable filter, a filter wheel, a gradient filter, or another suitable type of filter.

Detector 112 is configured to detect electromagnetic waves in a spectrum emitted by emitter 102 and convert the detected electromagnetic waves into an electrical signal. In some embodiments, detector 112 is a charge-coupled device (CCD) detector, a complimentary metal-oxide-semiconductor (CMOS) detector, a photodiode array, or other suitable detector elements.

Electromagnetic inspection tool 100 is usable at many points throughout a semiconductor production process. In some embodiments, electromagnetic inspection tool 100 is used on a blank wafer prior to processing of the wafer to identify any defects inherent in the wafer. In some embodiments, electromagnetic inspection tool 100 is used after each processing step to increase quality control and more easily identify a location of problems which arise during production. In some embodiments, electromagnetic inspection tool 100 is used after several processing steps in order to increase throughput of the production process.

In some embodiments, every processed wafer is inspected using electromagnetic inspection tool 100 to maximize quality control. In some embodiments, less than every processed wafer is inspected using electromagnetic inspection tool 100 in order to increase throughput of the production process.

Inspection using electromagnetic inspection tool 100 is more rapid than an e-beam inspection process. In a non-limiting example of a 300 mm wafer, an e-beam inspection process used to inspect an entirety of the wafer would take about 20 days to about 30 days to complete. In contrast, electromagnetic inspection of the 300 mm wafer is able to be completed in about 1 hour.

Figure 2A:
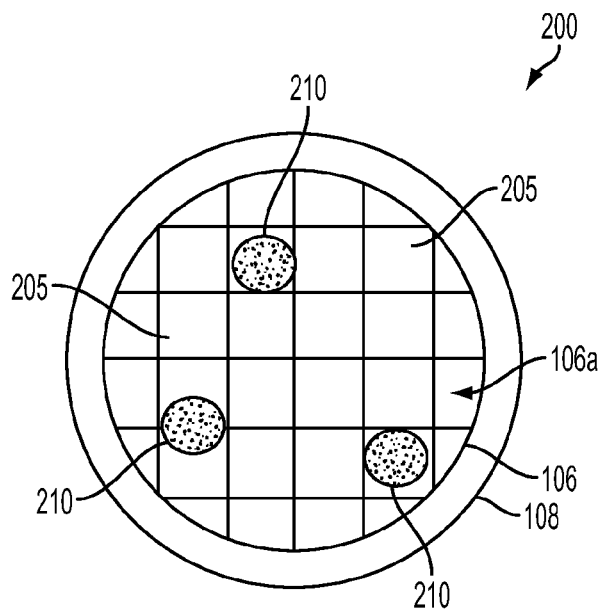
FIG. 2A is a diagram of a location specific inspection scheme in accordance with one or more embodiments.

FIG. 2A is a diagram of a location specific inspection scheme 200 in accordance with one or more embodiments. Wafer 106 includes a plurality of dies 205 arrayed on surface 106a. Location specific inspection scheme 200 includes a number of distinct locations 210 for inspection. In some embodiments, locations 210 are randomly selected. In some embodiments, locations 210 are selected based on historical abnormality information. Historical abnormality information includes information regarding locations where abnormalities occur most often in a specific production process. In some embodiments, a user selects locations 210. Location specific inspection scheme 200 includes three locations 210 for inspection. In some embodiments, a number of locations 210 for inspection is greater than or less than three. In some embodiments, at least one location 210 overlaps adjacent dies 205 to provide information related to a die edge.

In some embodiments, emitted electromagnetic waves 104 are translated relative to wafer 106 in order to inspect locations 210. In some embodiments, emitted electromagnetic waves 104 are translated by moving an optical element within emitter 102, e.g., a movable mirror, a movable lens, a movable prism, or other suitable adjustable optical element. In some embodiments, emitter 102 is translated with respect to wafer 106 to translate emitted electromagnetic waves 104 across surface 106a. In some embodiments, stage 108 is configured to translate wafer 106 relative to emitter 102. In some embodiments, stage 108 is configured to translate wafer 106 using at least one of a piezoelectric motor, a rack and pinion system, or another suitable translation element.

Figure 2B:
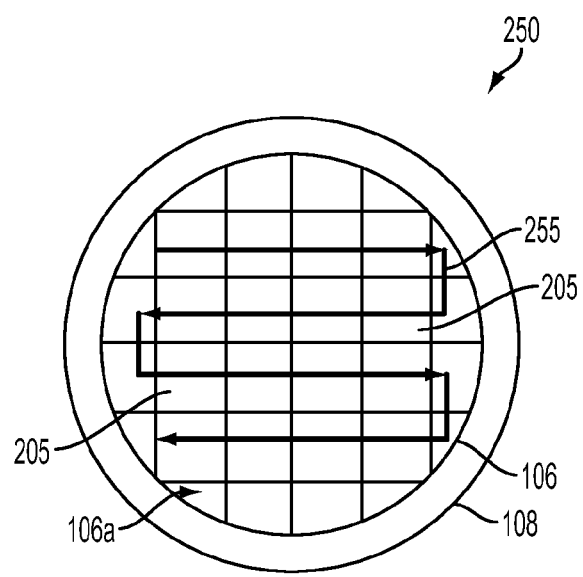
FIG. 2B is a diagram of a scanning inspection scheme in accordance with one or more embodiments.

FIG. 2B is a diagram of a scanning inspection scheme 250 in accordance with one or more embodiments. Wafer 106 includes a plurality of dies 205 arrayed on surface 106a.

Scanning inspection scheme 250 inspects the plurality of dies 205 in a pattern along an inspection path 255. Scanning inspection scheme 250 includes inspection path 255 proceeding along an entire row of dies 205 and then proceeding to a subsequent row of dies 205. In some embodiments, inspection path 255 has a different pattern, e.g., a diagonal path, scanning less than an entirety of a row, skipping a row, or another suitable inspection path. In some embodiments, inspection path 255 is determined based on historical abnormality information. In some embodiments, a user determines inspection path 255. Scanning inspection scheme 250 includes a single inspection path 255. In some embodiments, a number of inspection paths 255 is greater than one. In some embodiments, at least one inspection path 255 traverses an area between adjacent dies 205 to provide information related to the die edge.

In some embodiments, a target location of emitted electromagnetic waves 104 is moved relative to wafer 106 during scanning inspection scheme 250. In some embodiments, stage 108 is configured to move wafer 106 relative to emitted electromagnetic waves 104 during scanning inspection scheme 250. In some embodiments, mechanisms for moving the target location emitted electromagnetic waves 104 or wafer 106 in scanning inspection scheme 250 are similar to those described with respect to location specific inspection process 200.

Figure 3A:
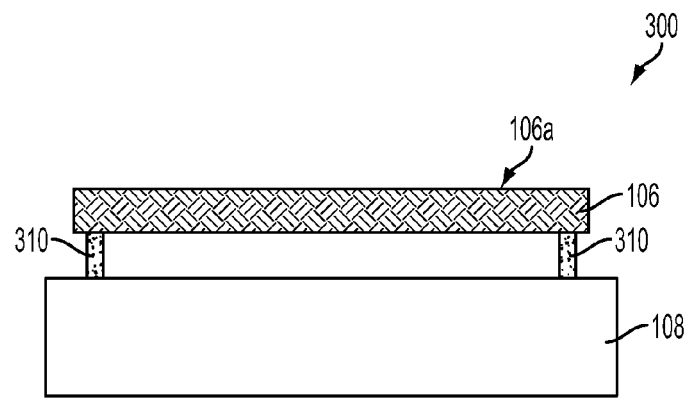
FIG. 3A is a side view of a pin charging arrangement in accordance with one or more embodiments.

FIG. 3A is a side view of a pin charging arrangement 300 in accordance with one or more embodiments. Pin charging arrangement 300 includes wafer 106 having surface 106a disposed over stage 108 and supporting the wafer. A plurality of pins 310 are positioned between wafer 106 and stage 108. Pins 310 are configured to transfer an electrical charge to wafer 106 and surface 106a to enhance contrast during optical inspection. Pins 310 comprise a conductive material. In some embodiments, pins 310 comprise aluminum, tungsten, gold, a conductive polymer or another suitable conductive material.

Pins 310 receive the electrical charge through stage 108 and transfer the electrical charge to wafer 106. In some embodiments, pins 310 are connected to a separate power source configured to provide an electrical charge to pins 310 for transfer to wafer 106.

Pins 310 have sufficient width to conduct the electrical charge without damaging the pins. The electrical charge transferred through pins 310 is sufficient to charge surface 106a to greater than 0 eV and in some embodiments as low as a 1 eV. In some embodiments, the electrical charge transferred through pins 310 is sufficient to charge surface 106a to about 1,000 eV to about 3,000 eV.

Figure 3B:
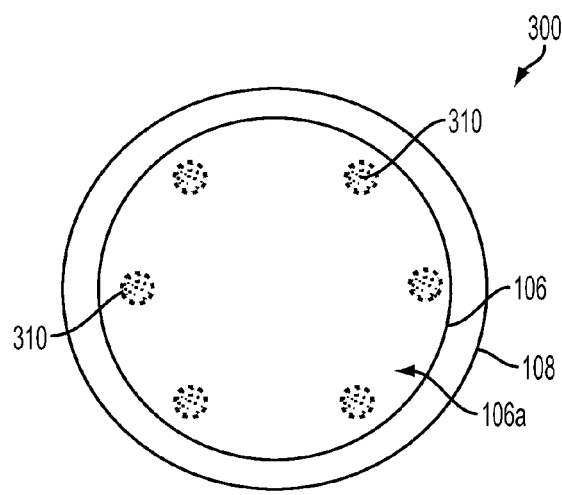
FIG. 3B is a top view of a pin charging arrangement in accordance with one or more embodiments.

As a number of layers on wafer 106 increases, the efficiency of charge transfer from pins 310 to surface 106a is reduced. In response to the decreased charge transfer efficiency, processing parameters for the electromagnetic inspection are adjusted. In some embodiments, a wavelength of the electromagnetic waves incident on surface 106a is changed. In some embodiments, a charging time is increased. In some embodiments, a charge supplied through pins 310 is increased. FIG. 3B is a top view of a pin charging arrangement 300 in accordance with one or more embodiments. Pins 310 are dispersed at various locations adjacent to an outer edge of wafer 106. In some embodiments, pins 310 are disposed uniformly across a surface of wafer 106, on opposite ends of the wafer, along sidewalls of the wafer, or other suitable locations with respect to the wafer. Pin charging arrangement 300 includes six pins 310. In some embodiments, a number of pins 310 is greater than or less than six. Pin charging arrangement 300 has pins 310 positioned at regular intervals. In some embodiments, pins 310 are spaced at irregular intervals.

Figure 4:
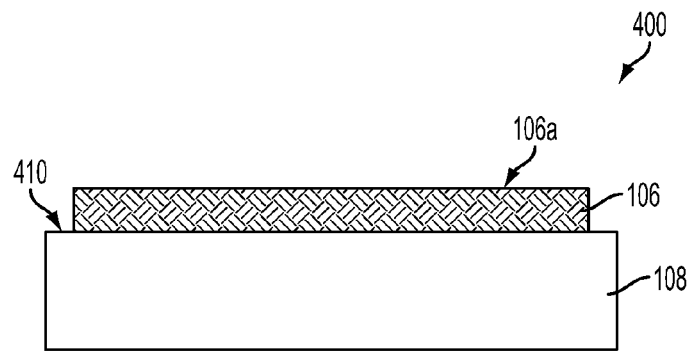
FIG. 4 is a side view of a direct contact charging arrangement in accordance with one or more embodiments.

FIG. 4 is a side view of a direct contact charging arrangement 400 in accordance with one or more embodiments. Direct contact charging apparatus 400 includes stage 108 in direct contact with wafer 106. Electrical charge is transferred directly from stage 108 to wafer 106. In some embodiments, the electrical charge is provided by a power source in stage 108. In some embodiments, stage 108 is electrically charged by a power source external to the stage. In some embodiments, an entire interface surface 410 of stage 108 at an interface between the stage and wafer 106 is conductive to transfer the electrical charge. In some embodiments, less than the entire interface surface 410 is conductive. In some embodiments, conductive portions of the interface surface 410 are spaced across stage 108 to provide an even charge distribution to wafer 106.

Stage 108 is configured to transfer sufficient electrical charge to charge surface 106a to the target level. In some embodiments, the target level is greater than 0 eV, and in some embodiments the target level is at least 1 eV. In some embodiments, stage 108 is configured to transfer sufficient electrical charge to charge surface 106a to a target level from about 1,000 eV to about 3,000 eV. In some embodiments, as the number of layers on wafer 106 increase, the process parameters of the electromagnetic inspection are adjusted.

Figure 5:
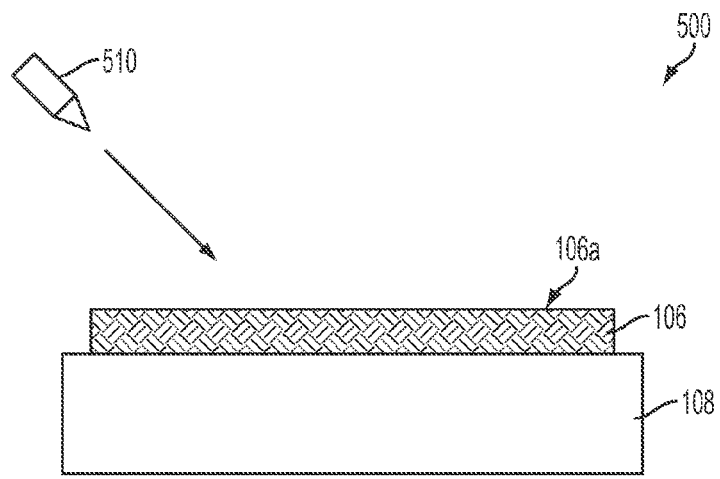
FIG. 5 is a side view of an electron gun charging arrangement in accordance with one or more embodiments.

FIG. 5 is a side view of an electron gun charging arrangement 500 in accordance with one or more embodiments. Electron gun charging arrangement 500 includes stage 108 supporting wafer 106 and an electron gun 510 configured to emit electrons at surface 106a. Electrical charge by emitting electrons from electron gun 510 onto surface 106a. Electron gun 510 is configured to transfer sufficient electrical charge to charge surface 106a to the target level, such as a target level greater than 0 eV or at least 1 eV. In some embodiments, electron gun 510 is configured to transfer sufficient electrical charge to charge surface 106a to the target level from about 1,000 eV to about 3,000 eV.

Figure 6:
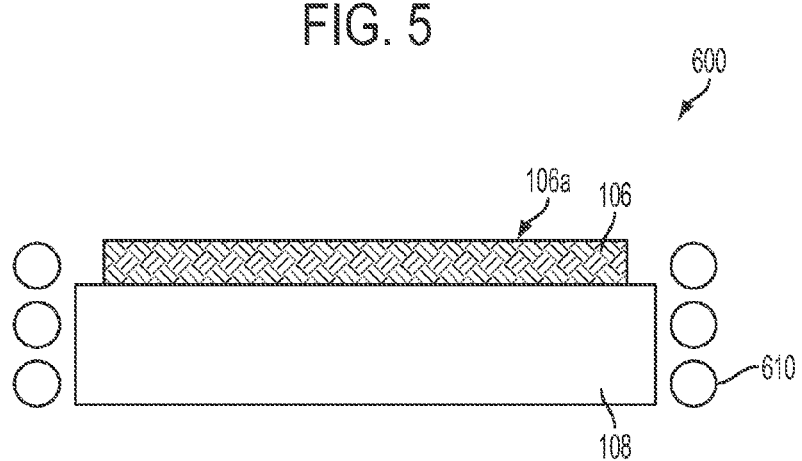
FIG. 6 is a side view of an induction charging arrangement in accordance with one or more embodiments.

A power of the electrons from electron gun 510 is sufficiently low to avoid damage to features on surface 106a; however, the power is sufficiently high to temporarily bind the electrons to the surface. In some embodiments, multiple electron guns 510 are employed to decrease a charging time for surface 106a FIG. 6 is a side view of an induction charging arrangement 600 in accordance with one or more embodiments. Induction charging arrangement 600 includes wafer 106 having surface 106a positioned on stage 108. An induction coil 610 is positioned surrounding wafer 106. In operation, a current is applied through induction coil 610 to induce charged elements, e.g., electrons or holes, present in wafer 106 to migrate to surface 106a. In some embodiments, induction coil 610 is configured to charge surface 106a to the target level, such as a target level greater than 0 eV or at least 1 eV. In some embodiments, induction coil 610 is configured to charge surface 106a to the target level ranging from 1,000 eV to about 3,000 eV.

Figure 7:
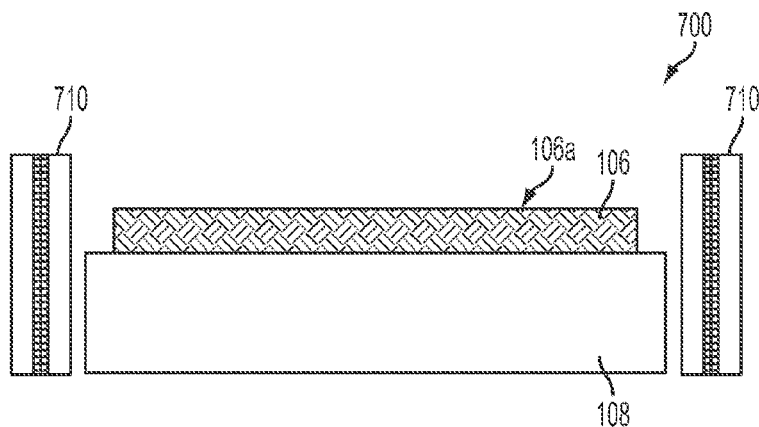
FIG. 7 is a side view of a capacitance charging arrangement in accordance with one or more embodiments.

FIG. 7 is a side view of a capacitance charging arrangement 700 in accordance with one or more embodiments. Capacitance charging arrangement 700 includes wafer 106 having surface 106a positioned on stage 108. At least one capacitor 710 is positioned adjacent to wafer 106. In operation, a charge is applied to capacitor 710 to induce charged elements, e.g., electrons or holes, present in wafer 106 to migrate to surface 106a. In some embodiments, capacitor 710 is configured to charge surface 106a to the target level, such as a target level greater than 0 eV or at least 1 eV. In some embodiments, capacitor 710 is configured to charge surface 160a to the target level ranging from 1,000 eV to about 3,000 eV.

Figure 8:
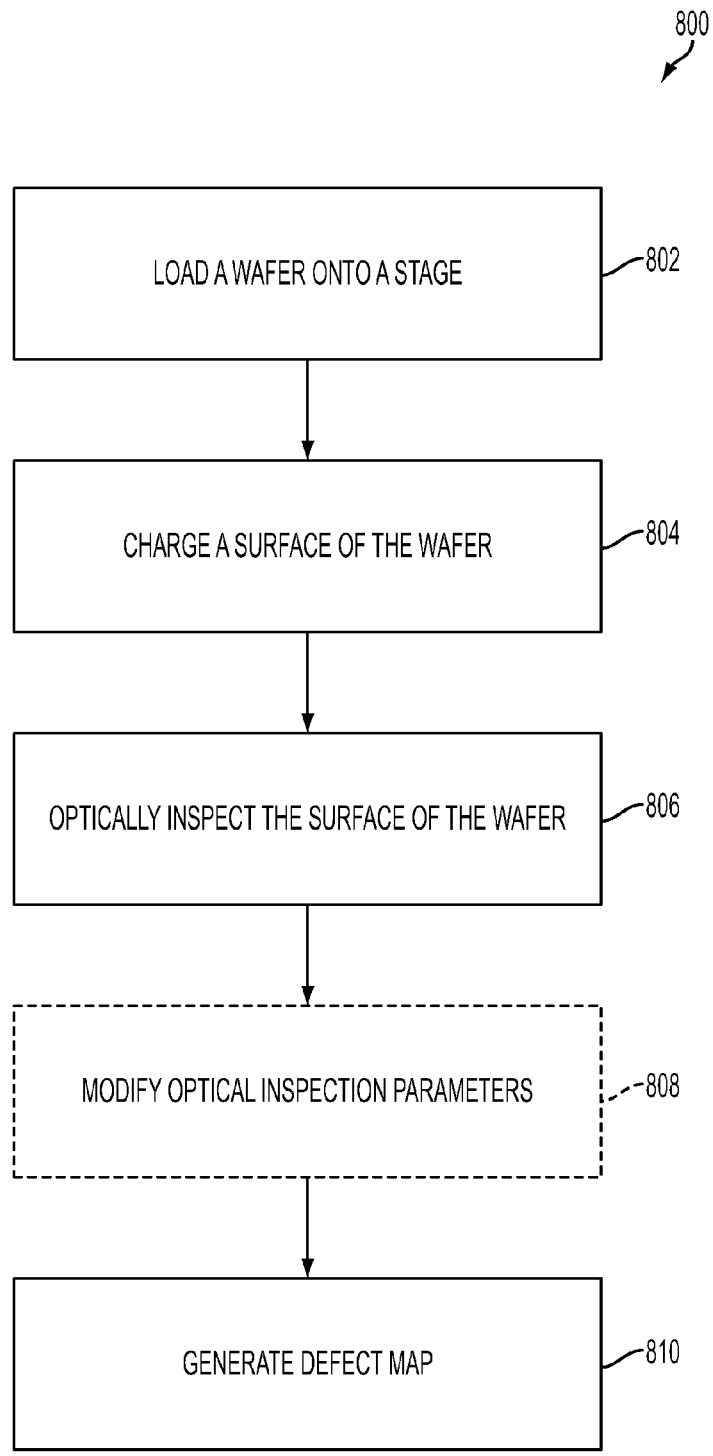
FIG. 8 is a flow chart of a method of using a wafer charging electromagnetic inspection tool in accordance with one or more embodiments.

FIG. 8 is a flowchart of a method 800 of using a wafer charging electromagnetic inspection tool in accordance with one or more embodiments. In operation 802, a wafer, e.g., wafer 106, is loaded onto a stage, e.g., stage 108. In some embodiments, the wafer is loaded onto the stage using a robotic arm to remove the wafer from a front-opening unified pod (FOUP) and place the wafer on the stage. In some embodiments, alignment marks or alignment surfaces are used to properly orient the wafer on the stage to facilitate electromagnetic inspection of selected locations.

In operation 804, a surface of the wafer is charged. The surface of the wafer is charged to a target level, such as a target level greater than 0 eV or at least 1 eV. In some embodiments, the surface of the wafer is charged to the target level from about 1,000 eV to about 3,000 eV. In some embodiments, the charge is a positive charge resulting from an increased number of holes at the surface, e.g., surface 106a. In some embodiments, the charge is a negative charge resulting from an increased number of electrons at the surface. In some embodiments, the surface is charged using a contact charging arrangement, such as pin charging, direct contact charging, electron gun charging or other charging methods configured to introduce electrons or holes onto the surface. In some embodiments, more than one contact charging arrangement is used simultaneously. In some embodiments, the surface is charged using a contact-less charging arrangement, such as induction charging, capacitance charging or other suitable charging arrangements configured to induce migration of charges within the wafer to the surface. In some embodiments, more than one contact-less charging arrangement is used simultaneously. In some embodiments, a combination of contact and contact-less charging arrangements are used simultaneously.

In operation 806, electromagnetic inspection of the wafer surface is performed using an electromagnetic inspection tool, e.g., electromagnetic inspection tool 100. Electromagnetic inspection is performed by using an emitter, e.g., emitter 102, to produce electromagnetic waves incident on the surface. The surface, e.g., surface 106a, either reflects, refracts, and/or scatters the incident electromagnetic waves. The reflected, refracted, and/or scattered incident electromagnetic waves are collected by a detector, e.g., detector 112. In some embodiments, the electromagnetic waves are in a DUV spectrum. In some embodiments, the electromagnetic waves are in an EUV spectrum. In some embodiments, the electromagnetic waves are in a visible spectrum.

In some embodiments, the wafer remains stationary during the electromagnetic inspection and the emitter moves relative to the wafer. In some embodiments, the emitter remains stationary during electromagnetic inspection and the wafer moves relative to the emitter. In some embodiments, both the wafer and the emitter move during electromagnetic inspection.

In some embodiments, the electromagnetic inspection involves imaging the surface at a plurality of specific locations on the wafer surface. In some embodiments, the specific locations are randomly selected. In some embodiments, the specific locations are selected based on historic abnormalities data. In some embodiments, the specific locations are selected by a user. In some embodiments, the specific locations overlap a plurality of dies on the wafer surface.

In some embodiments, the electromagnetic inspection involves scanning the surface. In some embodiments, all dies on the surface are scanned. In some embodiments, less than all the dies on the surface are scanned.

In optional operation 808, electromagnetic inspection parameters are modified. In some embodiments, a single electromagnetic inspection tool, e.g., electromagnetic inspection tool 100, is used for electromagnetic inspection following several different processing steps. Electromagnetic inspection parameters for inspecting a wafer following a first process are not optimal for inspecting the wafer following a different second process. As a result, electromagnetic parameters are adjusted in order to obtain a higher contrast for the detected signal. In some embodiments, the electromagnetic parameters which are adjusted include a wavelength of the emitted electromagnetic waves, e.g., emitted electromagnetic waves 104; a focal length of the emitter, e.g., emitter 12; an aperture of the emitter; reflected or refracted inspection of the wafer surface; a charging time; and/or a surface charge on the wafer. In some embodiments, operation 808 is omitted if the electromagnetic inspection tool has already been calibrated for inspection following a specific process. In some embodiments, operation 808 occurs prior to operation 806. In some embodiments, operations 806 and 808 are performed in a recursive manner in order to maximize a contrast of the detected signal.

In operation 810, a defect map is generated. A detector, e.g., detector 112, receives electromagnetic waves from the wafer surface and converts the electromagnetic waves into an electrical signal. The electrical signal is transmitted to a computer which generates the defect map using a processor. In some embodiments, the computer is part of a metrology apparatus, or another suitable computer. The defect map contains information regarding a type of abnormality and a location of the abnormality on a surface of the wafer.

One aspect of this description relates to an electromagnetic inspection tool. The electromagnetic inspection tool includes a stage configured to support a wafer having a first surface and an emitter configured to emit electromagnetic waves to be incident on the first surface. The electromagnetic inspection tool further includes a detector configured to detect electromagnetic waves returned from the first surface and a charging mechanism configured to charge the first surface.

Another aspect of this description relates to a method of electromagnetically inspecting a wafer. The method includes loading a wafer having a first surface onto a stage and emitting electromagnetic waves to be incident on the first surface. The method further includes detecting electromagnetic waves returned from the first surface and charging the first surface prior to detecting the electromagnetic waves returned from the first surface.

It will be readily seen by one of ordinary skill in the art that the disclosed embodiments fulfill one or more of the advantages set forth above. After reading the foregoing specification, one of ordinary skill will be able to affect various changes, substitutions of equivalents and various other embodiments as broadly disclosed herein. It is therefore intended that the protection granted hereon be limited only by the definition contained in the appended claims and equivalents thereof.

What is claimed is:
1. An electromagnetic inspection tool comprising:
a stage configured to support a wafer having a first surface;
an emitter configured to emit electromagnetic waves to be incident on the first surface;

a detector configured to detect electromagnetic waves returned from the first surface and to output a detection signal based on the electromagnetic waves returned from the first surface; and an induction device positioned along a side of the stage perpendicular to the first surface of the stage configured to support the wafer, wherein the detection signal has a contrast, and the induction device is configured to selectively adjust the contrast of the detection signal based on an amount of charge induced onto the first surface.

2. The electromagnetic inspection tool of claim 1, wherein the induction device is configured to induce a charge onto the first surface that changes a charge level of the first surface by at least one electron volt (eV).

3. The electromagnetic inspection tool of claim 1, wherein the emitter is configured to emit electromagnetic waves in an ultraviolet spectrum.

4. The electromagnetic inspection tool of claim 1, wherein the emitter and the detector are positioned relative to the stage to detect electromagnetic waves reflected from the first surface.

5. The electromagnetic inspection tool of claim 1, wherein the emitter and the detector are positioned relative to the stage to detect electromagnetic waves refracted or scattered from the first surface.

6. The electromagnetic inspection tool of claim 1, wherein the induction device is a contact-less charging arrangement.

7. The electromagnetic inspection tool of claim 6, wherein the contact-less charging arrangement is an inductive charging arrangement, wherein the electromagnetic inspection tool further comprises:

an induction coil configured to surround the wafer and induce a migration of charge to the first surface.

8. The electromagnetic inspection tool of claim 6, wherein the contact-less charging arrangement is a capacitance charging arrangement, wherein the electromagnetic inspection tool further comprises:

at least one capacitor configured to be positioned adjacent to the wafer and induce a migration of charge to the first surface.

9. A method of electromagnetically inspecting a wafer, the method comprising:

loading a wafer having a first surface onto a stage;
emitting electromagnetic waves toward the first surface;
detecting electromagnetic waves returned from the first surface;
generating a detection signal based on the electromagnetic waves returned from the first surface; and
charging the first surface from a lateral side of the stage prior to detecting the electromagnetic waves returned from the first surface to a selected charge level, wherein the detection signal has a contrast, and charging the first surface to the selected charge level causes the contrast of the detection signal to change.

10. The method of claim 9, wherein charging the first surface comprises inducing a charge onto the first surface that changes the charge level of the first surface by at least one electron volt (eV).

11. The method of claim 9, wherein charging the first surface comprises providing a charge to a second surface of the wafer opposite the first surface.

12. The method of claim 9, wherein charging the first surface comprises emitting electrons toward the first surface using an electron gun.

13. The method of claim 9, wherein charging the first surface comprises using an induction coil surrounding the wafer to induce charge migration in the wafer toward the first surface.

14. The method of claim 9, wherein charging the first surface comprises using at least one capacitor adjacent to the wafer to induce charge migration in the wafer toward the first surface.

15. The method of claim 9, further comprising:
detecting a plurality of distinct locations on the first surface.

16. The method of claim 9, further comprising:
scanning the electromagnetic waves across the first surface.

17. An electromagnetic inspection tool comprising:
a stage configured to support a wafer;
an induction device positioned surrounding sidewalls of the stage, wherein the induction device is configured to induce a migration of charge in the wafer;
an emitter configured to emit electromagnetic waves to be incident on the wafer; and
a detector configured to detect electromagnetic waves returned from the wafer and to output a detection signal based on the electromagnetic waves returned from the wafer;
wherein the detection signal has a contrast corresponding to an amount of charge induced onto the wafer.

18. The electromagnetic inspection tool of claim 17, wherein the induction device comprises an induction coil configured to surround the wafer and induce the migration of charge to the wafer.

19. The electromagnetic inspection tool of claim 17, wherein the induction device comprises at least one capacitor configured to be positioned adjacent to the wafer and induce the migration of charge to the wafer.

20. The electromagnetic inspection tool of claim 17, wherein the induction device is configured to selectively adjust the contrast of the detection signal based on the amount of charge induced in the wafer.

* * * * *